United States Patent [19]

Walter

[11] 4,137,260

[45] Jan. 30, 1979

[54] PROCESS FOR PRECIPITATION OF CARBOXYALKOXY SUCCINATE TETRAHYDRATE SALT

[75] Inventor: Thomas J. Walter, Baton Rouge, La.

[73] Assignee: Ethyl Corporation, Richmond, Va.

[21] Appl. No.: 765,214

[22] Filed: Feb. 3, 1977

[51] Int. Cl.$^2$ ............................................. C07C 59/23
[52] U.S. Cl. ................................. 562/580; 260/501.17
[58] Field of Search ........................ 260/535 P, 501.17

[56] References Cited

U.S. PATENT DOCUMENTS

| | | | |
|---|---|---|---|
| 3,965,169 | 6/1976 | Stahlweber | 260/535 P |
| 4,014,929 | 3/1977 | Stahlheber | 260/535 P |
| 4,014,930 | 3/1977 | Feiler et al. | 260/535 P |

Primary Examiner—Paul J. Killos
Attorney, Agent, or Firm—Donald L. Johnson; John F. Sieberth; Paul H. Leonard

[57] ABSTRACT

It is disclosed that water soluble carboxyalkoxy succinate tetrahydrate salt can be precipitated in high purity from alcohol-water solvent systems when operating at temperatures from about 50° C to about 100° C using seed crystals of either tetrahydrate or pentahydrate form or a mixture thereof. Useful temperatures are from about 45° to about 75° C. Preferred temperatures are above about 55° C up to about 65° C where tetrahydrate product is obtainable even where pentahydrate seed is used.

15 Claims, No Drawings

PROCESS FOR PRECIPITATION OF CARBOXYALKOXY SUCCINATE TETRAHYDRATE SALT

BACKGROUND OF THE INVENTION

1. Field of the Invention

This invention relates in general to the preparation of water soluble salts of carboxyalkoxy succinic acids and in particular to the preparation of said salts in solid particulate form with controllable production of high purity tetrahydrate salt.

2. Description of the Art

It is known that water soluble salts of carboxyalkoxy succinic acids are useful detergent builder materials as disclosed in U.S. Pat. No. 3,635,830. The preparation of such materials is described in U.S. Pat. No. 3,914,297.

Where the receovery of salts from alcoholic aqueous solutions has been considered in the past, generally it has been desired to carry out the process at a low temperature, e.g. room temperature or 25°–30° C to minimize alcohol losses by evaporation, to avoid the need for pressure equipment and to minimize combustion hazards.

Carboxymethoxy succinic acid salts, for example, are readily produced by reacting salts of glycolic acid and maleic acid in an aqueous medium in the presence of enough zinc or alkaline earth metal hydroxide typically, calcium hydroxide, to produce a salt system having a pH of at least about 8 and preferably higher than about 11 when measured at 25° C. The reaction is preferably conducted at reflux temperature at about atmospheric pressure for from about 1 to about 6 hours. To produce water soluble salts, typically the calcium salt system is reacted with an alkali metal carbonate such as sodium or potassium carbonate at a moderate temperature of about 60° C and filtered to remove by-product calcium carbonate to yield an aqueous solution containing trisodium carboxymethoxy succinate or tripotassium carboxymethoxy succinate as appropriate. Such solutions can also be produced in other ways such as by converting the zinc or alkaline earth metal salt into acid by ion exchange or treatment with mineral acid and then reacting the carboxyalkoxy succinic acid with an organic or inorganic base to produce other water soluble salts typified herein such as alkali metal, ammonium, or alkanol ammonium salts.

Recovery of water soluble carboxymethoxy succinic acid salts in particulate form from aqueous solutions containing them is difficult, especially on a commercial scale. The usual or frequent result of attempting to recover particulate solid salt from solution by simple procedure as for example by crystallization and drum drying or by spray drying to remove water is the production of a mixture of hydrates which is excessively contaminated with undesirably large quantities of residual reactants an by-product materials.

None of the known prior art describes a suitable process that can be used on a commercial scale for recovering a uniform particulate tetrahydrate product substantially devoid of free water. Especially is it evident that none of the open literature describes how one may obtain selectively tetrahydrate salts of alkali metal carboxyalkoxy succinic acids which are desirable in that they contain less water of hydration than corresponding pentahydrate salts. As far as is known, no open literature teaches how to control the course of precipitation of salts of carboxyalkoxy succinic acids from alcoholic aqueous solution so as to obtain substantially pure tetrahydrate salt. As a matter of fact, the open literature does not even appreciate the tetrahydrate-pentahydrate mixture problem, much less attempt to provide a solution to it.

SUMMARY OF THE INVENTION

As discussed in the foregoing, the preparation of solutions of alkali metal and other water soluble salts of carboxyalkoxy succinic acid is readily accomplished in any of several ways. A preferred way for producing a preferred salt is by reacting salts of glycolic acid and maleic acid in an aqueous medium in the presence of an alkaline earth metal hydroxide such as calcium hydroxide to produce an intermediate calcium salt of carboxymethoxy succinic acid. The calcium salt can be reacted with an alkali metal or other appropriate salt capable of contributing a highly soluble cation, typically sodium carbonate, to produce a solution of water soluble salt of carboxyalkoxy succinic acid and by-product calcium carbonate which are separated albeit not without difficulty. The resulting solution of carboxyalkoxy succinic acid salt can be combined with detergent materials and the mixture thus obtained used as a liquid or dried in some manner as by spray drying so as to produce a dry product. As a practical matter, however, water soluble carboxyalkoxy succinic acid salts usually are produced at a point which is remote from the point at which the combination with detergent materials is accomplished. Thus, it is desirable to produce a form of "dry" or particulate salt for detergent use which can be shipped at minimum expense, requiring the recovery of such salt from the aqueous solution. The recovery is complicated by the fact that water soluble carboxyalkoxy succinic acid salts have several hydrate forms containing different amounts of water. It is important to maintain uniformity in this regard otherwise detailed analysis and ratio adjustments are required with each new shipment. It is to this general problem area that the present application is directed to which end it is sought to provide a process whereby one can obtain the tetrahydrate salt uniformly and consistently over a period of time in many different batches or periods of operation.

In accordance with the present invention a process is provided for producing predominantly tetrahydrate alkali metal, ammonium or amine salt of carboxyalkoxy succinic acid from an aqueous solution containing said salt which comprises forming a supersaturated system by combining said solution with (1) lower alkanol having from 1 to about 3 carbon atoms per molecule, and (2) tetrahydrate, pentahydrate or mixed tetrahydrate and pentahydrate seed, said system containing from about 30 to about 65 percent by weight of alcohol, from about 20 to about 50 percent by weight of water and from about 10 to about 30 percent salt, maintaining a system temperature of from about 45 to about 75° C for a finite period wherein precipitation occurs, and recovering a precipitate of salt from said system.

Preferably the temperature is from about 50° to about 70° C, especially from about 55° to about 65° C, typically about 55° C. Preferably the seed is tetrahydrate salt and the temperature is from about 55° to about 65° C.

Preferably the alcohol content of the system is from about 35 to about 50 percent by weight, especially from about 40 to about 48 percent by weight, typically about 45 percent by weight.

Preferably the water content of the system is from about 30 to about 45 percent by weight, especially from about 32 to about 40 percent, typically about 35 percent by weight.

Preferably the salt content of the system is from about 15 to about 25 percent by weight, especially from about 17 to about 23 percent by weight, typically about 20 percent by weight.

In a preferred embodiment, the temperature is about 55° C, the alcohol content of the system is about 45 percent by weight, the water content of the system is about 35 percent by weight and the salt content of the system is about 20 percent by weight.

Preferably the salt is an alkali metal salt of carboxymethoxy succinic acid, especially sodium salt of carboxymethoxy succinic acid.

Preferably the alkanol is methanol. In a preferred embodiment, the salt is the tetrahydrate of trisodium carboxymethoxy succinic acid and the alcohol is methanol.

In a preferred aspect, the present invention relates to a process for the selective crystallization of a predominantly tetrahydrate water soluble sodium-, potassium- or ammonium salt of a carboxyalkoxy succinic acid of the general formula

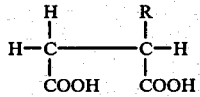

wherein R is a carboxyalkoxy radical (—OR'COOH) having from 2 to about 7 carbon atoms total, R' is a divalent, straight chain alkyl structure [—$(CH_2)_n$—] where $n$ is 1–6, in particulate form from an aqueous solution of the salt, characterized in that the solution is combined with methanol and at least an effective amount of a seed of tetrahydrate salt or pentahydrate salt or mixture of said tetrahydrate and pentahydrate salt of said acid, in that a temperature of from about 55° to about 65° C is employed during crystallization of the product, in that the alcohol content of the combined system is from about 40 to about 48 percent by weight, the water content of the combined system is from about 32 to about 40 percent by weight and the salt content of the system is from about 17 to about 23 percent by weight. Preferably the temperature is about 55° C, the alcohol content of the system is about 45 percent by weight, the water content of the system is about 35 percent by weight and the salt content of the system is about 20 percent by weight.

DISCUSSION

Generally, the salts of the present invention are water soluble salts useful as builders being salts of acids which have the formula:

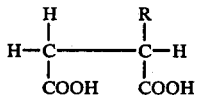

wherein R is a carboxyalkoxy radical (—OR'COOH) having from 2 to about 7 carbon atoms total, R' preferably being a "divalent, straight chain alkyl" structure [—$(CH_2)_n$—] where $n$ is 1–6. Examples of such acids are α-carboxymethoxy succinic acid, α-(1-carboxybutoxy) succinic acid, α-(2-methyl-3-carboxybutoxy) succinic acid, α-(1-carboxyhexoxy) succinic acid, α-carboxyisobutoxy succinic acid, and the like. A preferred acid has been found to be the above mentioned α-carboxymethoxy succinic acid because the alkali metal and other water soluble salts thereof are readily produced at low cost and are effective and useful detergent builders.

Typical useful water soluble salts of α-carboxymethoxy succinic acid are the alkali metal, the ammonium and the lower alkanol ammonium salts having from 2 to about 6 carbon atoms in the alkanol structure such as sodium salts, potassium salts, ammonium salts, triethanol ammonium salts, diethanol ammonium salts, monoethanol ammonium salts, monoisopropanol ammonium salts, mono-n-butanol ammonium salts, and the like and mixtures of two or more thereof.

Preferred salts are the sodium, potassium and ammonium salts, with the sodium salts being particularly preferred because of low cost, effectiveness and ease of production.

The builders of this invention can be used to advantage with a wide variety of detergent actives or surfactants, including those known in the art as anionic, cationic, nonionic, ampholytic, and zwitterionic detergents as well as any suitable mixture of such detergents. Included also are soaps such as those of natural or synthetic origin coconut and tallow range soaps of straight chain or branched chain carbon skeleton structures.

Typical detergent mixtures contain the builders of this invention with or without one or more other builders such as salts of other polycarboxylic acids, typically oxydisuccinic acid, nitrilotriacetic acid, phosphoric acid, tartaric acid, tetrahydrofuran tetracarboxylic acid, citric acid; plus one or more of the conventional actives such as alkyl benzene sulfonates, olefin sulfonates, sulphobetaines, alkanol sulfates, alkanol alkoxy sulfates, amides, amine oxides and the like. When the resultant washing compositions are used in aqueous washing systems, the cleaning power of the formulation is enhanced in much the same way as when the commonly used alkali metal polyphosphate salt builders are employed as the only builders. Yet the present builder systems do not contribute to or magnify the eutrophication problems characteristic of phosphorus-containing builders. The builders of the present invention are generally used in formulations containing other agents such as abrasives, dyes, perfumes, anti-redeposition agents, pH modifiers, inorganic salts such as sodium chloride, lime-soap dispersants, brighteners, bacteriostats, water hardness additives, and the like.

Typical salts are:
sodium carboxymethoxy succinate
potassium carboxymethoxy succinate
ammonium carboxymethoxy succinate
monoethanolammonium carboxymethoxy succinate
diethanolammonium carboxymethoxy succinate
triethanolammonium carboxymethoxy succinate
sodium carboxyethoxy succinate
potassium carboxyethoxy succinate
ammonium carboxyethoxy succinate
monoethanolammonium carboxyethoxy succinate
diethanolammonium carboxyethoxy succinate
triethanolammonium carboxyethoxy succinate
sodium carboxypropoxy succinate
sodium carboxybutoxy succinate
sodium carboxypentoxy succinate
sodium carboxyhexoxy succinate The foregoing salts exist in various hydrated forms with various amounts (mols) of water of hydration per mol of hydrated salt.

Typical alkanols are methanol, ethanol, isopropanol and normal propanol. Preferred is methanol because of its outstanding solubility characteristics, its low cost and ready availability.

Numerous detergent compounds useful with the builders produced in accordance with the present process are described in "Surface Active Agents" by Schwartz and Perry, Interscience Publishers, Inc., New York 1949.

For rapid crystallization the use of seed crystals is preferred in the present process. The attainment of high purity product is facilitated by the use of the same kind of salt as the desired product; however, one of the advantages of the present process is that the hydrate form of the seed is not critical. Thus high purity tetrahydrate product can be obtained with the present process under the preferred conditions, especially about 55° C, regardless of whether the seed is tetrahydrate, pentahydrate or a mixture of the two. The amount of seed is not critical but in general one uses only an adequate or effective amount to achieve the desired results. In general the amount of seed ranges from about 0.01 to about 10 percent of the amount of salt in the system. Typical amounts of salt are a "pinch", viz., two to three milligrams, per five to ten grams of salt in the system.

In general, the proportions set forth, especially the most preferred conditions, result in the formation of systems which become quite thick as crystallization progresses. Thus it is usually preferred to begin the crystallization under proportions as set forth in the ranges herein using corresponding amounts of initial alcohol, and after crystallization has progressed, to supply additional alcohol to facilitate stirring and removal of mother liquor so as to accomplish the removal of co-present impurities. In general, the amount of additional alcohol supplied is not critical. It can of course be zero, yet on the other hand, the use of large amounts of alcohol is not desired for obvious reasons. In general, one will use a ratio of additional alcohol to initial alcohol ranging from about 1:10 to about 10:1, a ratio of about 1:1 being typical and usually preferred.

As indicated, the additional alcohol is generally added after the major portion of crystallization has occurred or at least initiated so that the hydrate form will have been established prior thereto. In addition, the additional alcohol can be added in one or more increments or continuously depending upon the circumstances to provide optimum operation.

The following examples indicate preferred embodiments and aspects of the present invention.

EXAMPLE 1

To a flask equipped with an agitator and a heater was added 20 grams of an aqueous solution of trisodium carboxymethoxy succinic acid salt. The solution contained 35 percent by weight of salt. The flask and contents were brought to the selected temperature of 55° C and 21 ml of methanol was added gradually over a five minute period.

Then 2 to 3 milligrams of crystalline trisodium carboxymethoxy succinic acid tetrahydrate salt was added to the flask. The system was stirred for 1 hour at 55° C, most of the crystallization occurring during this period. As crystallization progressed, the system became quite thick. To facilitate stirring, additional methanol was then added to make a total of 46 ml of methanol added.

The system was stirred for an additional 30 minutes at 55° C, cooled to room temperature (25°-30° C), then filtered at room temperature. The crystals recovered were then washed at room temperature with 6 ml methanol, the crystals air dried for 2 hours at room temperature, then oven dried at 50° C to a constant weight. The product was analyzed for hydrate form by X-ray diffraction pattern analysis.

The product was high purity tetrahydrate of highly crystalline form.

EXAMPLES 2 TO 16

Example 1 was repeated under various conditions in a series of runs. Results are presented in Table I. Where the product is reported as amorphous, it is indicated that this is likely to be small crystals of the same hydrate form distribution as listed in the table.

At an early point in the comparative study, it was recognized that the most difficult test of the present process was the ability to form a tetrahydrate product when using a pentahydrate seed. Thus most of the examples used pentahydrate seed.

The more significant comparative results are evident from Examples 1–4 at temperatures of 55°–65° C against Examples 11–15 at room temperature (25°–30° C). The results of Example 16 apparently are anomalous. Where the product is identified as a "mixture", this usually means 10–15 percent of one crystalline form, the designation "mostly" generally referring to less than 10 percent of one crystalline form.

It is noted that the quantity of alcohol reported in the third column of the table is the amount that enters into the system proportions as defined in the claims. The bulk of the crystallization occurs in the presence of this initial amount of alcohol.

The starting salt solution used in Examples 3, 4, 5, 10, 13, 14 and 16 contained 27.3 wt. percent trisodium carboxymethoxy succinic acid salt, 4.6 wt. percent of other sodium organic salts and 68.1 wt. percent water. The starting salt solution used in Examples 6–9 and 15 contained 22.3 wt. percent trisodium carboxmethoxy succinic acid salt, 2.4 wt. percent of other sodium organic salts and 75.2 wt. percent water.

TABLE I

| Example | Starting CMOS Solution (Wt % CMOS) | Initial Methanol (ml) | Temp. | Seed (Hydrate form) | Product Hydrate Form | Crystallinity |
| --- | --- | --- | --- | --- | --- | --- |
| 1 | 35 | 21 | 55 | Tetra | Tetra | Highly crystalline |
| 2 | 35 | 21 | 55 | Penta | Tetra | Highly crystalline |
| 3 | 27.3 | 26 | 55 | Penta | Tetra | Highly crystalline |
| 4 | 27.3 | 26 | 65 | Penta | Tetra | 40–50% amorphous |
| 5 | 27.3 | 21 | 55 | Penta | Mostly tetra | <20% amorphous |
| 6 | 22.3 | 30 | 55 | Penta | Mostly tetra | Highly crystalline |
| 7 | 22.3 | 26 | 55 | Penta | Mostly tetra | <10% amorphous |
| 8 | 22.3 | 21 | 55 | Penta | Mostly tetra | ≈40% amorphous |
| 9 | 22.3 | 21 | 55 | Penta | Mostly tetra | ≈50% amorphous |
| 10 | 27.3 | 26 | 45 | Penta | Mostly tetra | 10–20% amorphous |
| 11 | 35 | 21 | Room Temp. | Tetra | Mostly tetra | 30–40% amorphous |

TABLE I-continued

| Example | Starting CMOS Solution (Wt % CMOS) | Initial Methanol (ml) | Temp. | Seed (Hydrate form) | Product Hydrate Form | Crystallinity |
|---|---|---|---|---|---|---|
| 12 | 35 | 21 | Room Temp. | Penta | Mostly penta | ≈50% amorphous |
| 13 | 27.3 | 26 | Room Temp. | Penta | Mostly tetra | ≈50% amorphous |
| 14 | 27.3 | 30 | Room Temp. | Penta | Mixture | Mostly amorphous |
| 15 | 22.3 | 30 | Room Temp. | Penta | Mixture | Mostly amorphous |
| 16 | 27.3 | 21 | 55 | Penta | Mixture | ≈50% amorphous |

I claim:

1. A process for producing predominantly tetrahydrate alkali metal, ammonium or amine salt of carboxyalkoxy succinic acid from an aqueous solution containing said salt which comprises forming a supersaturated system by combining said solution with (1) lower alkanol having from 1 to about 3 carbon atoms per molecule, and (2) tetrahydrate, pentahydrate or mixed tetrahydrate and pentahydrate seed, said system containing from about 30 to about 65 percent by weight of alcohol, from about 20 to about 50 percent by weight of water and from about 10 to about 30 percent salt, maintaining a system temperature of from about 45 to about 75° C for a finite period wherein precipitation occurs, and recovering a precipitate of predominantly tetrahydrate salt from said system.

2. The process of claim 1 wherein the temperature is from about 50° to about 70° C.

3. The process of claim 1 wherein the temperature is from about 55° to about 65° C.

4. The process of claim 1 wherein the temperature is about 55° C.

5. The process of claim 1 wherein the seed is tetrahydrate salt and the temperature is from about 55° to about 65° C.

6. The process of claim 1 wherein the alcohol content of the system is from about 35 to about 50 percent by weight.

7. The process of claim 6 wherein the water content of the system is from about 30 to about 45 percent by weight.

8. The process of claim 1 wherein the alcohol content of the system is from about 40 to about 48 percent by weight, the water content of the system is from about 32 to about 40 percent by weight and the salt content of the system is from about 17 to about 23 percent by weight.

9. The process of claim 1 wherein the temperature is about 55° C, the alcohol content of the system is about 45 percent by weight, the water content of the system is about 35 percent by weight and the salt content of the system is about 20 percent by weight.

10. The process of claim 1 wherein the salt is an alkali metal salt of carboxymethoxy succinic acid.

11. The process of claim 1 wherein the salt is a sodium salt of carboxymethoxy succinic acid.

12. The process of claim 1 wherein the salt is the tetrahydrate of trisodium carboxymethoxy succinic acid and the alcohol is methanol.

13. The process of claim 1 wherein the alkanol is methanol.

14. A process for the selective crystallization of a predominantly tetrahydrate water soluble sodium-, potassium- or ammonium salt of a carboxyalkoxy succinic acid of the general formula

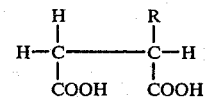

wherein R is a carboxyalkoxy radical (—OR'COOH) having from 2 to about 7 carbon atoms total, R' is a divalent, straight chain alkyl structure [—(CH$_2$)$_n$—] where $n$ is 1-6, in particulate form from an aqueous solution of the salt, characterized in that the solution is combined with methanol and at least an effective amount of a seed of tetrahydrate salt or pentahydrate salt or mixture of said tetrahydrate and pentahydrate salt of said acid, in that a temperature of from about 55 to about 65° C is employed during crystallization of the product, in that the alcohol content of the combined system is from about 40 to about 48 percent by weight, the water content of the combined system is from about 32 to about 40 percent by weight and the salt content of the system is from about 17 to about 23 percent by weight.

15. The process of claim 14 wherein the temperature is about 55° C, the alcohol content of the system is about 45 percent by weight, the water content of the system is about 35 percent by weight and the salt content of the system is about 20 percent by weight.

* * * * *